United States Patent
Kano et al.

(10) Patent No.: US 9,978,234 B2
(45) Date of Patent: May 22, 2018

(54) METHOD FOR MANUFACTURING HOUSING OF RADIATION DETECTION CASSETTE

(71) Applicant: FUJIFILM Corporation, Tokyo (JP)

(72) Inventors: Shinichi Kano, Ashigarakami-gun (JP); Hisatsugu Horiuchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 15/615,897

(22) Filed: Jun. 7, 2017

(65) Prior Publication Data
US 2017/0372572 A1 Dec. 28, 2017

(30) Foreign Application Priority Data

Jun. 27, 2016 (JP) .................................. 2016-126604

(51) Int. Cl.
| | |
|---|---|
| *G08B 13/19* | (2006.01) |
| *A61B 6/00* | (2006.01) |
| *G01T 1/24* | (2006.01) |
| *G03B 42/04* | (2006.01) |

(52) U.S. Cl.
CPC ............ *G08B 13/19* (2013.01); *A61B 6/4283* (2013.01); *G01T 1/244* (2013.01); *A61B 6/4258* (2013.01); *G03B 42/04* (2013.01)

(58) Field of Classification Search
CPC ....... G08B 13/19; G01T 1/244; A61B 6/4258; G03B 42/04
See application file for complete search history.

(56) References Cited

U.S. PATENT DOCUMENTS

| | | | | |
|---|---|---|---|---|
| 2,709,223 A | * | 5/1955 | Bachelder | G03B 42/04 378/183 |
| 5,720,389 A | * | 2/1998 | Yamazaki | B65D 25/10 206/316.1 |
| 2012/0219114 A1 | * | 8/2012 | Iwakiri | G03B 42/04 378/62 |

FOREIGN PATENT DOCUMENTS

JP      2011-084818 A      4/2011

OTHER PUBLICATIONS

Communication dated Nov. 30, 2017 from the European Patent Office in counterpart European application No. 17174153.1.

* cited by examiner

*Primary Examiner* — David Porta
*Assistant Examiner* — Faye Boosalis
(74) *Attorney, Agent, or Firm* — Sughrue Mion, PLLC

(57) ABSTRACT

Provided is a method for manufacturing a housing of a radiation detection cassette that can appropriately form a recess without a housing material depositing on an end mill or the like, in a case where a recess is formed by working the housing material formed of an alloy containing Mg and Li. A method for manufacturing a housing of a radiation detection cassette that houses a radiation detector in the housing includes preparing a housing material that is formed of an alloy containing Mg and Li and contains 0.1 mass % or more of Li, forming a recess using a working method other than cutting work on a surface of the housing material, and performing cutting work on the formed recess to shape the recess.

36 Claims, 7 Drawing Sheets

METHOD FOR MANUFACTURING HOUSING OF RADIATION DETECTION CASSETTE

CROSS-REFERENCE TO RELATED APPLICATIONS

The present application claims priority under 35 U.S.C. § 119 to Japanese Patent Application No. 2016-126604, filed on Jun. 27, 2016. Each of the above application(s) is hereby expressly incorporated by reference, in its entirety, into the present application.

BACKGROUND OF THE INVENTION

1. Field of the Invention

The present invention relates to a method for manufacturing a housing of a radiation detection cassette that houses a radiation detector within the housing.

2. Description of the Related Art

In the related art, radiation detection cassettes have been widely used in radiation imaging, such as X-ray imaging. The radiation detection cassettes are portable radiation detection devices including a rectangular housing, and a radiation detector that is housed within the housing and detects radiation transmitted through a subject.

The radiation detection cassettes are capable of being used by being attached to a stationary imaging stand where a subject is imaged in a standing posture or lying posture. In addition, the radiation detection cassettes are used by being put on a bed in order to image a site (for example, limbs) where imaging is difficult in the stationary imaging stand or by being carried by the subject himself or herself. Additionally, in order to image elderly people under recuperation at home or emergency cases due to an accident, disaster, or the like, the radiation detection cassettes may be used by being carried to the outside of hospitals without equipment of the imaging stand.

SUMMARY OF THE INVENTION

Here, the housing of the related-art radiation detection cassettes include a transmission plate that is arranged on a radiation exposure side and that allows radiation to be transmitted therethrough, and a back surface plate that is arranged to face the transmission plate. For example, an Mg alloy consisting of Mg (magnesium), Al (aluminum), and Zn (zinc) is used as the back surface plate.

Since the radiation detection cassettes are carried by a person, it is desirable that the radiation detection cassettes are light-weight, and it is desirable to use an alloy containing Mg and Li (lithium) whose specific gravity is smaller than that of the above Mg alloy (for example, refer to JP2011-084818A).

Meanwhile, recesses partitioned by ribs or the like are formed in an inner surface of the back surface plate. In a case where the recesses are formed by cutting work, it is necessary to perform grooving using an end mill or the like on a material in which no recesses are formed.

However, in a case where such grooving is performed, since an escape places for the heat of a blade of the end mill is small, the blade is heated, and the alloy containing Mg and Li whose melting point is lower than the above Mg alloy deposits on the blade of the end mill. As a result, the recess cannot be formed appropriately.

In view of the above problems, an object of the invention is to provide a method for manufacturing a housing of a radiation detection cassette that can appropriately form a recess without a housing material depositing on an end mill or the like, in a case where a recess is formed by working the housing material formed of an alloy containing Mg and Li.

Means for Solving the Problems

According to an aspect of the invention, there is provided a method for manufacturing a housing of a radiation detection cassette that houses a radiation detector in the housing. The method comprises preparing a housing material that is formed of an alloy containing Mg and Li and contains 0.1 mass % or more of Li, forming a recess using a working method other than cutting work on a surface of the housing material, and performing cutting work on the formed recess to shape the recess.

Additionally, the method for manufacturing a housing of a radiation detection cassette of the above invention, press working can be used as the working method other than the cutting work.

Additionally, the method for manufacturing a housing of a radiation detection cassette of the above invention, electrical discharge machining can be used as the working method other than the cutting work.

Additionally, the method for manufacturing a housing of a radiation detection cassette of the above invention, casting can be used as the working method other than the cutting work.

Additionally, in the method for manufacturing a housing of a radiation detection cassette of the invention, it is preferable that the housing material containing Li of 5 mass % or more and 25 mass % or less is prepared.

Additionally, in the method for manufacturing a housing of a radiation detection cassette of the invention, it is preferable that the housing material containing Al is prepared.

Additionally, in the method for manufacturing a housing of a radiation detection cassette of the invention, it is preferable that the housing material containing Al of 1 mass % or more and 12 mass % or less is prepared.

Additionally, in the method for manufacturing a housing of a radiation detection cassette of the invention, it is preferable that the housing material containing Ca is prepared.

Additionally, in the method for manufacturing a housing of a radiation detection cassette of the invention, it is preferable that housing material containing Ca of 0.3 mass % or more and 7 mass % or less is prepared.

Additionally, in the method for manufacturing a housing of a radiation detection cassette of the invention, it is preferable that a frame body is engaged with a circumferential edge of the housing material so as to protrude further outward than a position of a side end of the housing material as seen from a radiation exposure side.

Additionally, in the method for manufacturing a housing of a radiation detection cassette of the invention, a frame body is engaged with a circumferential edge of the housing material, and a water-proof structure is provided between the housing material and the frame body.

Additionally, in the method for manufacturing a housing of a radiation detection cassette of the invention, a side peripheral surface part of an inclined surface is formed in the housing material.

Advantage of the Invention

According to the method for manufacturing a housing of a radiation detection cassette of the invention, the method comprises preparing the housing material that is formed of the alloy containing Mg and Li and contains 0.1 mass % or more of Li, forming the recess using the working method other than cutting work on the surface of the housing material, and performing the cutting work on the formed recess to shape the recess. That is, the recess pattern is shaped by performing the working method other than cutting work before the cutting work is performed. Thus, it is not necessary to carry out grooving in the subsequent cutting work, and the final recess is shaped by shouldering. Hence, since the heat of a blade of an end mill can be dissipated, the recess can be appropriately shaped by without the material depositing on the blade of the end mill.

DESCRIPTION OF THE PREFERRED EMBODIMENTS

Figure 1:
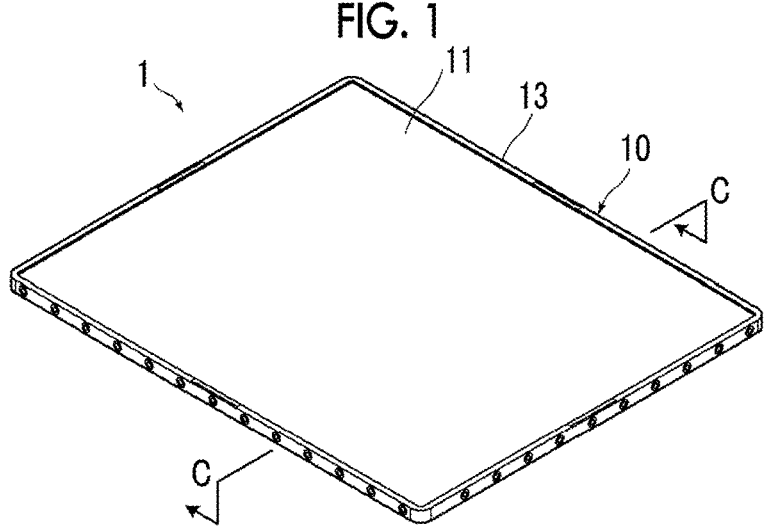
FIG. 1 is a perspective view illustrating the external appearance when an embodiment of a radiation detection cassette of the invention is seen from a radiation exposure side.
Figure 2:
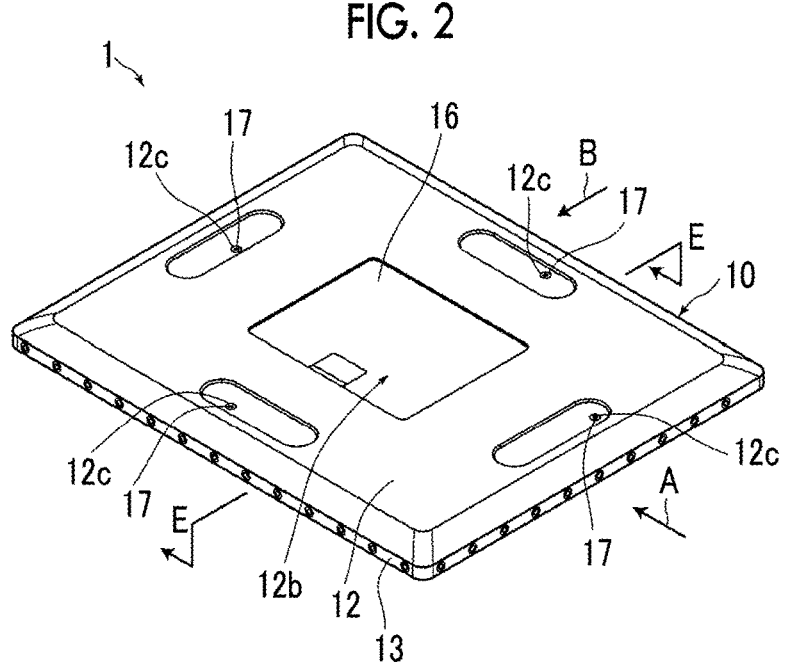
FIG. 2 is a perspective view illustrating the external appearance when the embodiment of the radiation detection cassette of the invention is seen from a side opposite to the radiation exposure side.
Figure 3:
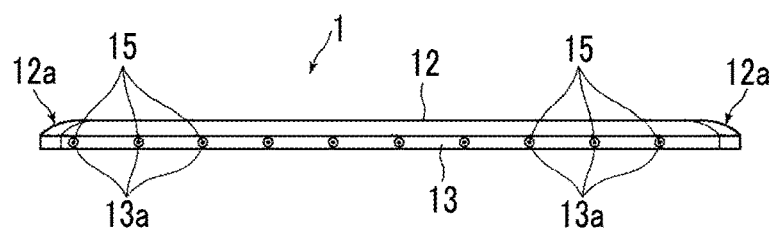
FIG. 3 is a view of the radiation detection cassette illustrated in FIG. 2 as seen from arrow A direction.
Figure 4:
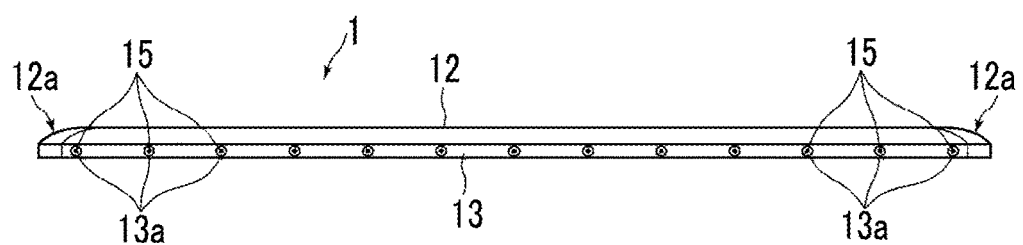
FIG. 4 is a view of the radiation detection cassette illustrated in FIG. 2 as seen from arrow B direction.

Hereinafter, an embodiment of a method for manufacturing a housing of a radiation detection cassette of the invention will be described in detail, referring to the drawings. Although the invention has features in the method for manufacturing a housing of a radiation detection cassette, the configuration of a radiation detection cassette having a housing manufactured using the embodiment of the manufacturing method of the invention will first be described. FIG. 1 is a perspective view illustrating the external appearance when the radiation detection cassette 1 having the housing manufactured by the manufacturing method of the present embodiment is seen from a radiation exposure side, and FIG. 2 is a perspective view illustrating the external appearance when the radiation detection cassette 1 is seen from a side opposite to the radiation exposure side. Additionally, FIG. 3 is a view of the radiation detection cassette 1 illustrated in FIG. 2 as seen from arrow A, and FIG. 4 is a view of the radiation detection cassette 1 illustrated in FIG. 2 as seen from arrow B.

The radiation detection cassette 1 of the present embodiment includes a radiation detector 20, and a housing 10 that houses the radiation detector 20.

As illustrated in FIGS. 1 to 4, the housing 10 is formed in a rectangular shape, and includes a transmission plate 11 arranged on the radiation exposure side, a back housing part 12 having a surface portion opposite to the radiation exposure side, and a frame body 13.

The transmission plate 11 is formed of a carbon material with a high transitivity of radiation, and is lightweight and high-rigidity.

The back housing part 12 is formed of an alloy containing Mg and Li and containing 0.1 mass % or more of Li. Since the alloy containing Mg and Li has a smaller specific gravity than an Mg alloy (Al 3%, Zn 1%, and Mg 96%) used as a material of a back housing part of the related-art radiation detection cassette, weight reduction of the radiation detection cassette 1 can be achieved. Additionally, the alloy containing Mg and Li has radiotransparency higher than the Mg alloy. Hence, generation of scattered radiation resulting from thickness structures, such as ribs formed on an inner surface (a surface on a radiation detector side) of the back housing part 12 can be suppressed. Accordingly, a radiation shield plate containing lead provided within the related-art radiation detection cassette to absorb the above scattered radiation can be thinned or omitted, and the weight reduction can be further achieved. As the alloy containing Mg and Li, for example, an alloy of 14 mass % of Li(s), 9 mass % of Al, and 77 mass % of Mg can be used. It is preferable that the content of Li is 5 mass % or more and 25 mass % or less. By making the content of Li be 25 mass % or less, manufacture can be made easy. Additionally, it is preferable that the content of Al is 1 mass % or more and 12 mass % or less. By making the content of Al be 1 mass % or more, corrosion resistance can be improved. Additionally, by making the content of Al be 12 mass % or less, the weight reduction can be achieved.

Additionally, as illustrated in FIGS. 3 and 4, the back housing part 12 has a side peripheral surface part 12a formed in a gentle inclined surface. By forming the side peripheral surface part 12a with an inclined surface In this way, for example, in a case where a radiation image of a subject that has lied oneself on a bed is captured, the radiation detection cassette 1 can be easily inserted between the subject and the bed.

Figure 5:
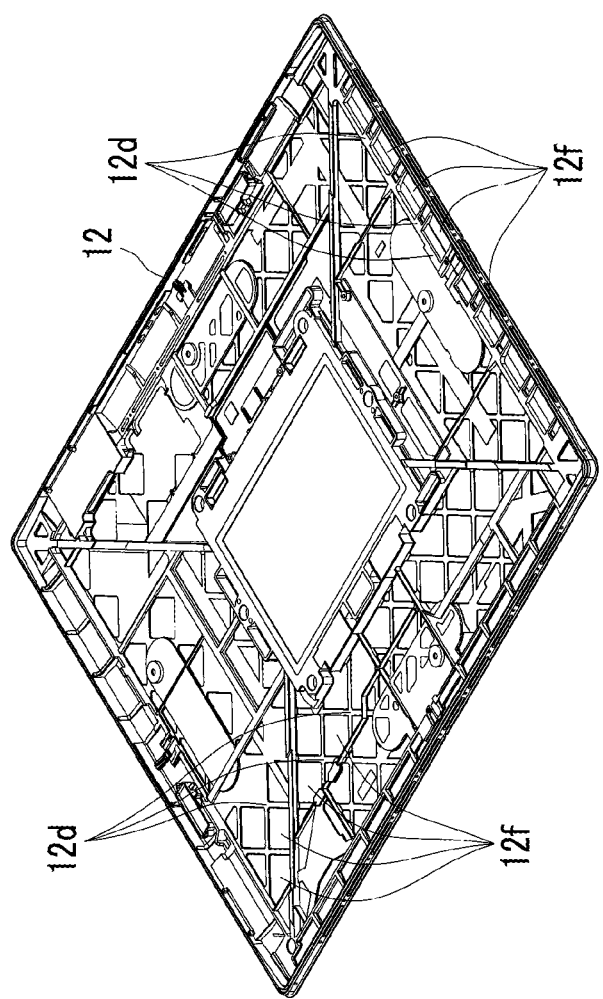
FIG. 5 is a perspective view of a back housing part formed of an alloy containing Mg and Li as seen from an inner surface (a surface on a radiation detector side) side.

Additionally, FIG. 5 is a perspective view of the back housing part 12 formed of the alloy containing Mg and Li as seen from the inner surface (the surface on the radiation detector side) side. As illustrated in FIG. 5, recesses 12f of various shapes partitioned off by ribs 12d are formed on an inner surface side of the back housing part 12. When such recesses 12f are formed, in the related art, the recesses 12f are formed by preparing a housing material in which no recesses 12f are formed and performing cutting work using an end mill or the like on the housing material.

Figure 6:
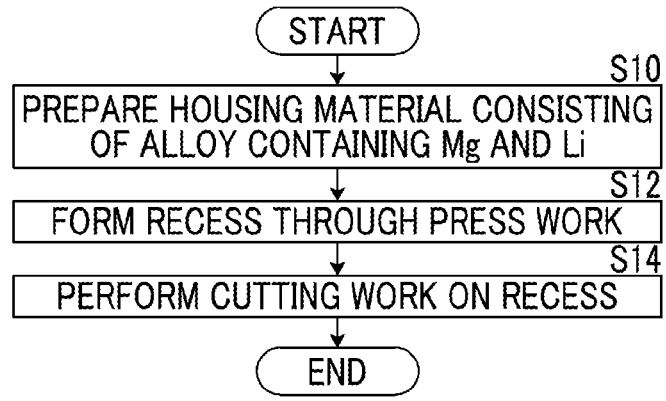
FIG. 6 is a flowchart for explaining an embodiment of a method for manufacturing a housing of the radiation detection cassette of the invention.

However, in a case where the back housing part 12 is formed of the alloy containing Mg and Li, as described above, the alloy may deposit on a blade of the end mill, so that the recesses cannot be appropriately machined. Thus, in the method for manufacturing a housing 10 of the present embodiment, the recesses 12*f* are formed through a flow illustrated in a flowchart illustrated in FIG. 6.

First, a housing material that is formed of the alloy containing Mg and Li and contains 0.1 mass % or more of Li is prepared (S10). Next, a rough recess pattern is formed by performing, for example, press working, such as hot pressing, on the surface of the housing material (S12).

Then, final recesses 12*f* are shaped by performing cutting work using an end mill or the like, on the recess pattern formed by the press working (S14).

According to the manufacturing method of an above embodiment, the rough recess pattern is shaped by performing the press working before the cutting work is performed. Thus, it is not necessary to carry out grooving in the subsequent cutting work, and the final recesses 12*f* are shaped by shouldering. Thus, the heat of the blade of the end mill can be dissipated. Accordingly, the recesses 12*f* can be appropriately shaped without the material depositing on the blade of the end mill.

In addition, in the present embodiment, the rough recess pattern is formed by performing the press working on the housing material before the cutting work. However, a working method before the cutting work is not limited to the press working, and the rough recess pattern may be formed using electrical discharge machining or casting, such as die casting.

Next, returning to FIG. 2, a battery housing part 12*b* in which a battery 16 that supplies electrical power to the radiation detector 20 is housed is formed in an outer surface of the back housing part 12. The battery housing part 12*b* is provided by forming a recess in the outer surface of the back housing part 12. In addition, FIG. 2 illustrates a state where the battery 16 is housed in the battery housing part 12*b*.

Additionally, female thread parts 12*c* are formed in the back housing part 12. A male thread 17 is fitted into each female thread part 12*c*, and thereby, members, such as a support member, which is housed within the housing 10, are fixed to the back housing part 12.

Here, although the back housing part 12 of the present embodiment is formed of the alloy containing Mg and Li as described above, the alloy containing Mg and Li tends to corrode electrically. That is, in a case where a different kind of metal comes into contact with the alloy containing Mg and Li, the alloy containing Mg and Li with large ionization tendency corrodes if electrolytes, such as water, act. Since medical instruments are disinfected and sterilized, the medical instruments are exposed to various electrolytes, such as ethanol and peracetic acid, besides water, and electrical corrosion poses a problem.

Hence, it is desirable that the male thread 17 fitted into the female thread part 12*c* made of the alloy containing Mg and Li is made of nonmetal, such as resin or ceramics.

Figure 7:
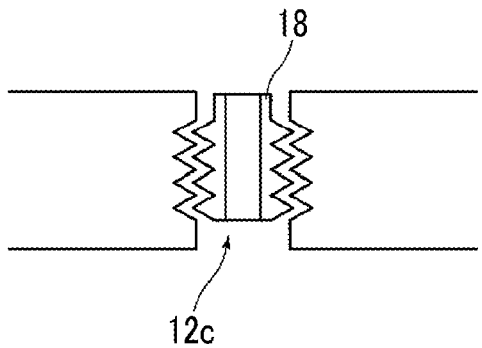
FIG. 7 is a view illustrating an insertion screw provided in a female thread part.

Additionally, a method of preventing the electrical corrosion of the female thread part 12*c* is not limited to this. For example, as illustrated in FIG. 7, a nonmetallic insertion screw 18 may be provided within the female thread part 12*c* such that the male thread is fitted into the insertion screw 18. Accordingly, even if a metallic male thread 17 is used, the male thread can be prevented from coming into direct contact with the female thread part 12*c*. The insertion screw 18 is grooved in a hole so as to be engaged with the male thread 17.

Otherwise, the processing of coating the inner surface of the female thread part 12*c* with a nonmetallic material may be performed. For example, in a case where chemical conversion treatment or the like is performed after the insertion screw 18 is inserted into the female thread part 12*c*, the electrical corrosion may occur between the female thread part 12*c* and insertion screw 18. However, by performing coating processing on the inner surface of the female thread part 12*c* as described above, the electrical corrosion between the female thread part 12*c* and the insertion screw 18 can also be prevented.

The frame body 13 is made of a metallic frame of which four corners are subjected to round chamfering. The frame body 13 is configured so as to be engaged with a circumferential edge of the back housing part 12. Additionally, the transmission plate 11 is fixed to the back housing part 12 by being engaged with the back housing part 12 in a state where the transmission plate 11 is fitted into the frame body 13.

Additionally, as illustrated in FIGS. 3 and 4, female thread parts 13*a* are formed in the frame body 13. Each female thread part 13*a* is formed through the frame body 13, and a male thread 15 is fitted into the female thread part. The male thread 15 fitted into the female thread part 13*a* of the frame body 13 reaches the back housing part 12, and is engaged with a female thread part (not illustrated) formed in the back housing part 12. Accordingly, the frame body 13 into which the transmission plate 11 is fitted is fixed to and integrated with the back housing part 12. In addition, in order to prevent the electrical corrosion resulting from contact with the female thread part of the back housing part 12, it is desirable that the male thread 15 is also made of nonmetal, such as resin or ceramics. Additionally, the invention is not limited to this. However, as described above, an insertion screw 18 may be provided in the female thread part formed in the back housing part 12, or coating processing may be performed on the inner surface of the female thread part formed in the back housing part 12.

Figure 8:
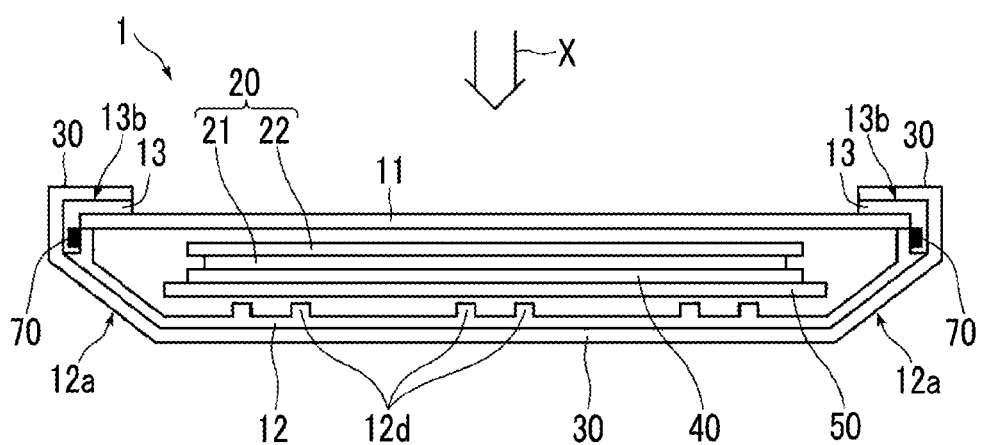
FIG. 8 is a C-C line cross-sectional view of the radiation detection cassette illustrated in FIG. 1.

FIG. 8 is a C-C line cross-sectional view of the radiation detection cassette 1 of FIG. 1. In addition, the cross-sectional view illustrated in FIG. 8 is a schematic view illustrating a schematic configuration of the radiation detection cassette 1, and the sizes of respective parts are not accurate.

As illustrated in FIG. 8, an outer surface of the back housing part 12 is provided with a protective film 30. In the present embodiment, as described above, the back housing part 12 is formed of the alloy containing Mg and Li. Accordingly, the weight reduction of the radiation detection cassette 1 can be achieved. On the other hand, however, since the radiation detection cassette 1 may be subjected to sterilization, disinfection, and the like or may be exposed to electrolyte solutions, such as a patient's blood, the corrosion resistance is required. The alloy containing Mg and Li is less resistant against corrosion than an Mg alloy containing no Li. Thus, in the present embodiment, the protective film 30 is provided as described above. Thus, improvement in the corrosion resistance can be achieved.

In addition, in the present embodiment, the entire outer surface of the back housing part 12 is provided with the protective film 30. However, the invention is not limited to this, and a portion of the outer surface of the back housing part 12 may be provided with the protective film 30. Specifically, the side peripheral surface part 12*a* of the back housing part 12 is a portion that comes into contact with a bed when the radiation detection cassette 1 is inserted between a subject and the bed. Hence, since the side peripheral surface part 12*a* of the back housing part 12, that is, a peripheral part of the surface of the housing 10 opposite to the radiation exposure side is worn due to contact with the bed, scratch resistance is required. Hence, it is desirable to provide the protective film 30 at least on the side peripheral surface part 12a of the back housing part 12. It is preferable that a range where the protective film 30 is provided is a range of 30 mm or more and 50 mm or less from a side end of the back housing part 12. By providing the protective film 30 in such a range, the weight reduction can be achieved as compared to a case where the protective film 30 is provided on the entire outer surface of the back housing part 12. Additionally, even in a case where the protective film 30 is provided on the entire outer surface of the back housing part 12, it is preferable to make the thickness of the protective film 30 in the side peripheral surface part 12a of the back housing part 12 larger than the thickness of the protective film 30 provided in ranges other than the above range.

Additionally, in the radiation detection cassette 1 of the present embodiment, as illustrated in FIG. 8, the protective film 30 is continuously provided from the outer surface of the back housing part 12 to an outer surface 13b of the frame body 13. The outer surface 13b of the frame body 13 on the radiation exposure side, that is, the peripheral part of the surface of the housing 10 on the radiation exposure side is a portion that comes into contact with a subject when the radiation detection cassette 1 is inserted between the subject and a bed. Therefore, since the outer surface 13b of the frame body 13 on the radiation exposure side is worn due to contact with the subject, the scratch resistance is required. Hence, it is desirable to provide the protective film 30 at least on the outer surface 13b of the frame body 13 on the radiation exposure side. It is desirable that the range where the protective film 30 is provided is provided in ranges other than a radiation detection region. Additionally, even in a case where the protective film 30 is provided on the entire outer surface 13b of the frame body 13 continuously from the outer surface of the back housing part 12, it is preferable to make the thickness of the protective film 30 in the outer surface 13b of the frame body 13 larger than the thickness of the protective film 30 provided in the other ranges.

As the protective film 30, it is desirable to use a resin sheet. The resin sheet has easy handling and pasting. As the resin sheet, for example, polyvinyl chloride sheets can be used. However, the protective film 30 is not limited to this. For example, the protective film 30 may be formed by performing phosphoric-acid-based or chromium-based chemical conversion treatment. Otherwise, the protective film 30 may be formed by plating, such as electroless plating or the like, or the protective film 30 may be formed by painting, such as solvent painting and powder coating. Additionally, in order to further improve the corrosion resistance, the protective film 30 may be made to contain Al.

Next, a schematic configuration within the housing 10 of the radiation detection cassette 1 will be described, referring to FIG. 8. As illustrated in FIG. 8, the radiation detector 20, a radiation shield plate 40, and a support 50 are provided within the housing 10 of the radiation detection cassette 1.

The radiation detector 20 is a rectangular detector that detects radiation transmitted through a subject. The radiation detector 20 of the present embodiment includes a scintillator layer (phosphor layer) 21 that converts incident radiation into visible light, and a thin film transistor (TFT) active matrix substrate 22 that photoelectrically converts of visible light emitted from the scintillator layer 21 to output radiation image signals. A rectangular imaging region where a plurality of pixels that accumulate electric charge according to the visible light from the scintillator layer 21 are arrayed is formed on the TFT active matrix substrate 22. In addition, in the present embodiment, the TFT active matrix substrate 22 and the scintillator layer 21 are arranged in this order from the radiation exposure side illustrated by arrow X in FIG. 8. However, the invention is not limited to this. Conversely, the scintillator layer 21 and the TFT active matrix substrate 22 are arranged in this order from the radiation exposure side.

Additionally, in addition to the radiation detector 20, an imaging control unit including a gate driver that gives a gate pulse to a gate of a TFT to switch the TFT, a signal processing circuit that converts an electric charge accumulated in a pixel to an analog electrical signal representing a radiation image to output the converted signal, and the like is provided within the housing 10.

Additionally, in the present embodiment, a so-called indirect conversion type radiation detector 20 that performs photoelectric conversion after radiation is first converted into visible light is used as the radiation detector 20. However, a so-called direct conversion type radiation detector that directly converts radiation into an electric charge signal may be used. Additionally, in the present embodiment, a so-called TFT reading type radiation detector using the TFT active matrix substrate 22 is used. However, the invention is not limited to this. A so-called optical reading type radiation detector that accumulates an electric charge with irradiation of radiation first and reads the stored charge with irradiation of excitation light to acquire a radiation image signal may be used.

The radiation shield plate 40 is provided on the side opposite to the radiation exposure side with respect to the radiation detector 20 within the housing 10, and is formed from a plate-like member containing lead with a thickness of more than 0 mm and less than 0.1 mm.

The radiation shield plate 40 absorbs the scattered radiation resulting from the thickness structures, such as ribs 12d formed on the inner surface of the back housing part 12. In the present embodiment, since the back housing part 12 is formed of the alloy containing Mg and Li as described above, the generation of the scattered radiation itself can be suppressed. Hence, the radiation shield plate 40 can be made thinner than that in the related art, and the weight reduction can be achieved. In addition, in the present embodiment, lead is used as the material of the radiation shield plate 40. However, the invention is not limited to this. Other radiation absorbent materials, such as Steel Use Stainless (SUS), iron, and tungsten, may be used.

The radiation shield plate 40 and the radiation detector 20 are bonded together, for example, using an adhesive tape or the like.

The support 50 supports the radiation detector 20 and the radiation shield plate 40, and is formed of a carbon material that allows radiation to be transmitted through. The support 50 of the present embodiment is fixed to the back housing part 12, and thereby, the radiation detector 20 and the radiation shield plate 40 are fixed to the back housing part 12.

Figure 9:
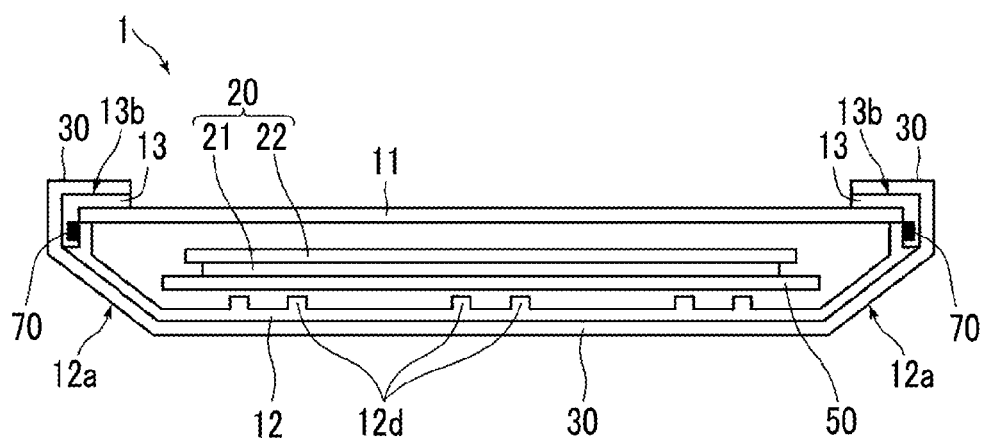
FIG. 9 is a cross-sectional view illustrating another embodiment of the radiation detection cassette of the invention.

In addition, in the present embodiment, the radiation shield plate 40 is provided as described above. However, the radiation shield plate 40 may be omitted. That is, as illustrated in FIG. 9, the support 50 and the inner surface of the back housing part 12 directly face each other without providing the radiation shield plate 40. In addition, the support 50 and the inner surface of the back housing part 12 directly facing each other means that other members are not present between the support 50 and the inner surface of the back housing part 12.

Figure 10:
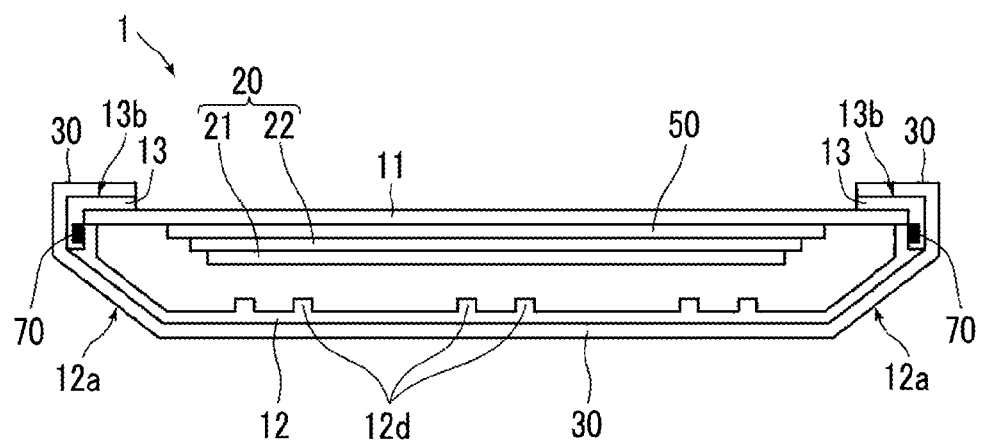
FIG. 10 is a cross-sectional view illustrating still another embodiment of the radiation detection cassette of the invention.

Additionally, the configuration in which the radiation shield plate 40 is not provided is not limited to the configuration illustrated in FIG. 9. As illustrated in FIG. 10, the support 50 may be fixed to the transmission plate 11 side and the radiation detector 20 may be provided at the support 50 such that the radiation detector 20 and the inner surface of the back housing part 12 directly face each other. In addition, the radiation detector 20 and the inner surface of the back housing part 12 directly facing each other means that other members are not present between the radiation detector 20 and the inner surface of the back housing part 12. Additionally, even in the configuration illustrated in FIGS. 7 and 8, the arrangement of the scintillator layer 21 and the TFT active matrix substrate 22 may be reversed.

Additionally, in the radiation detection cassette 1 of the present embodiment, as illustrated in FIG. 8, a waterproof structure 70 may be provided in a gap of a portion where the circumferential edge of the back housing part 12 and the frame body 13 are engaged with each other. As the waterproof structure 70, for example, rubber packing can be used. The rubber packing is crushed by the engagement between the circumferential edge of the back housing part 12 and the frame body 13, so that liquid-tight sealing can be made, and liquids, such as water, ethanol, and peracetic acid, which are used for disinfection and sterilization can be prevented from entering the housing 10.

Additionally, in a case where the radiation detection cassette 1 of the above embodiment is installed and used on a bed or is installed and used on an imaging stand for standing position imaging, the radiation transmitted through the radiation detection cassette 1 may be reflected to structures, such as the bed or the imaging stand, to enter the radiation detector 20 within the radiation detection cassette 1, and an artifact may be generated. Hence, in order to prevent the generation of such an artifact, a radiation shield 60 containing lead may be provided at a position on the side opposite to the radiation exposure side of the radiation detection cassette 1.

It is preferable that this radiation shield 60 is made attachable and detachable with respect to the housing 10. By adopting such a configuration, the radiation shield 60 can be attached to the housing 10 if necessary. In a case where there is no necessity, by detaching the radiation shield 60 from the housing 10, the weight reduction of the radiation detection cassette 1 can be achieved, and carrying is also easy.

Figure 11:
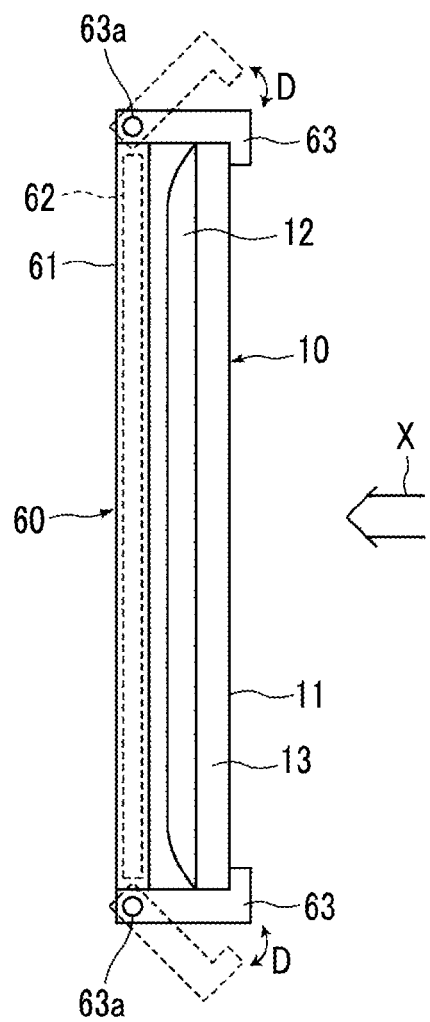
FIG. 11 is a view illustrating an example of a radiation shield that is attachably and detachably configured with respect to the housing of the radiation detection cassette.

FIG. 11 is a view illustrating an example of a radiation shield 60 that is attachable to and detachable from the housing 10. The radiation shield 60 includes a radiation shield plate 62 containing lead, a housing part 61 in which the radiation shield plate 62 is housed, and an attachment member 63. In addition, a direction of arrow X illustrated in FIG. 11 is a radiation exposure direction.

As the radiation shield plate 62, for example, a plate made of lead and having a thickness of 0.5 mm in the radiation exposure direction can be used. In addition, radiation absorbent materials such as a plate made of SUS and having a thickness of 1.5 mm in the radiation exposure direction, a plate made of tungsten and having a thickness of 1.5 mm in the radiation exposure direction, or a plate made of iron and having a thickness of 2.0 mm in the radiation exposure direction can be used.

Attachment members 63 are respectively provided on sides that faces the housing part 61. Each attachment member 63 is turned in a direction of arrow D about a turning shaft 63a. Each attachment member 63 is engaged with each of the sides that face the housing 10 of the radiation detection cassette 1, and thereby, the radiation shield 60 is attached to the housing 10 of the radiation detection cassette 1. FIG. 9 illustrates a state where the radiation shield 60 is attached to the housing 10, and illustrates a state of the attachment members 63 in a case where the radiation shield 60 is detached from the housing 10, by a dotted line.

By attaching the attachment members 63 to the radiation shield 60 side like a configuration illustrated in FIG. 11, it is not necessary to perform special processing on the housing 10 of the radiation detection cassette 1. Hence, since it is possible to be attached to any type of housing 10 if the size of the radiation shield 60 matches the size of the housing 10, it is not necessary to customize the radiation detection cassette 1, and reduction of cost can be achieved. However, as the configuration in which the radiation shield 60 is attachable and detachable, the invention is not limited to the configuration illustrated in FIG. 11, and other configurations may be adopted.

Additionally, as a method of suppressing the artifact resulting from the radiation being reflected due to the bed, the imaging stand, or the like, the protective film 30 may be made to contain lead, and the protective film 30 may be made to absorb the radiation reflected due to the bed, the imaging stand, or the like. In this case, it is preferable that the thickness of the protective film 30 is about 0.2 mm, and it is preferable that lead contains about 50 mass %.

Additionally, in the radiation detection cassette 1 of the above embodiment, the protective film 30 is provided in order to give the corrosion resistance and the scratch resistance as described above. However, it is still more preferable to make the protective film 30 has a fireproof enclosure function. Specifically, it is preferable that the protective film 30 contains at least one of Ca, B, and metal. For example, in a case where the resin sheet is used as the protective film 30, a resin sheet containing at least one of Ca (calcium), B (boron), and the metal may be used. Otherwise, in a case where a paint film is used as the protective film 30, metal may be contained in a paint material. As the metal contained in the protective film 30, there is, for example, Ca or the like.

Additionally, in a case where the protective film 30 is made to have the fireproof enclosure function as described above, it is desirable to provide the protective film 30 on the entire outer surface of the back housing part 12. However, in the radiation detection cassette 1 of the present embodiment, the battery housing part 12b where a battery is housed is formed in the back housing part 12 as described above. Thus, for example, in a case where the resin sheet is used as the protective film 30, it is difficult to laminate the resin sheet uniformly within the battery housing part 12b and at the peripheral part of the battery housing part 12b.

Figure 12:
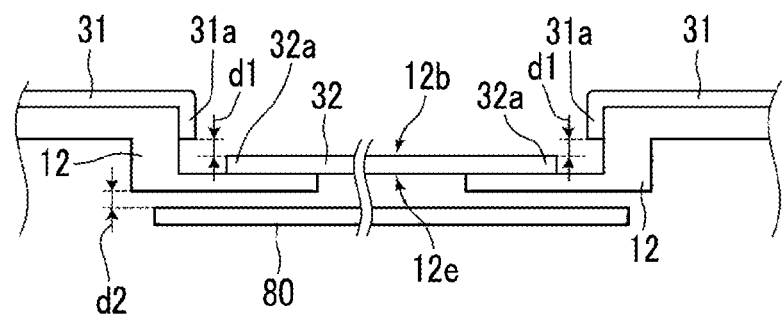
FIG. 12 is a cross-sectional view illustrating a schematic configuration around a recess formed in the back housing part.

Then, it is preferable to laminate separate resin sheets within the battery housing part 12b and at the peripheral part of the battery housing part 12b. FIG. 12 is a view illustrating a sectional view, taken along arrow E-E line, of the battery housing part 12b and its peripheral part of the radiation detection cassette 1 illustrated in FIG. 2. In addition, in FIG. 12, the battery 16 installed within the battery housing part 12b is not illustrated. As illustrated in FIG. 12, it is preferable to provide a first protective film 31 at the peripheral part of the battery housing part 12b and provide a second protective film 32 at a bottom part of the recess. It is preferable that a gap d1 between an end part 31a of the first protective film 31 and an end part 32a of the second protective film 32 adjacent to the end part 31a is more than 0 mm and 2 mm or less. Otherwise, the end part 31a of the first protective film 31 and an end part 32a of the second protective film 32 may be made to overlap each other as seen from the side opposite to the radiation exposure side.

Additionally, for the weight reduction of the back housing part 12, as illustrated in FIG. 12, it is preferable to form an opening 12e at the bottom part of the battery housing part 12b. Since the opening 12e being provided in this way is not good from a viewpoint of electro-magnetic compatibility (EMC), in the related-art radiation detection cassette, this opening is not provided, or the opening is needed to be closed using a sheet member.

In contrast, in the radiation detection cassette 1 of the present embodiment, the alloy containing Mg and Li is used as a material of the back housing part 12. Thus, EMC is improved compared to a case where the related-art Mg alloy is used. Hence, it is not necessary to provide the sheet member as in the related-art radiation detection cassette, and as illustrated in FIG. 12, a medium plate 80 serving as the support member can be arranged near the opening 12e. The medium plate 80 is formed of metal. It is preferable that a gap d2 between the opening 12e and the medium plate 80 is more than 0 mm and 2 mm or less.

Additionally, the alloy of the back housing part 12 instead of the protective film 30 may be made to contain Ca. It is preferable that the content of Ca is 0.3 mass % or more and 7 mass % or less. By making the content of Ca be 0.3 mass % or more, flame retardance can be improved. Additionally, the weight reduction can be achieved by making the content of Ca be 7 mass % or less. As the alloy containing Ca, for example, an alloy of 14 mass % of Li, 9 mass % of Al, 1 mass % of Ca, and 76 mass % of Mg can be used.

Additionally, both the alloy of the back housing part 12 and the protective film 30 may be made to contain Ca.

Figure 13:
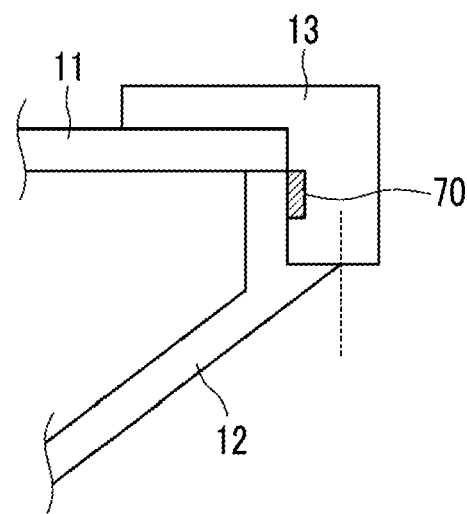
FIG. 13 is a view illustrating still another embodiment of a frame body that constitutes the housing.

Additionally, it is preferable that the radiation detection cassette 1 of the above embodiment includes the frame body 13. However, as illustrated in FIG. 13, it is preferable that the frame body 13 is formed so as to protrude further outward than a position (a position illustrated by a dotted line in FIG. 13) at a side end of the back housing part 12 as seen from the radiation exposure side. By adopting such a configuration, for example, the impact resistance when the radiation detection cassette 1 has fallen on the ground can be improved.

Additionally, as a method of improving the impact resistance of the radiation detection cassette 1, in a case where the protective film 30 is formed of the paint film, it is preferable that a cushioning property is provided by making the paint thickness be 50 μm or more. Additionally, two or more layers of paint films may be formed, and the total thickness thereof may be 50 μm or more. Additionally, in a case where the resin sheet is used as the protective film 30, it is preferable to use a resin sheet of 50 μm or more.

Additionally, regarding the protective film 30 of the radiation detection cassette 1 of the above embodiment, it is preferable to perform water-repellent coating processing or water-repellent painting. Accordingly, the corrosion resistance can be further improved.

EXPLANATION OF REFERENCES

- 1: radiation detection cassette
- 2: radiation detector
- 10: housing
- 11: transmission plate
- 12: back housing part
- 12a: side peripheral surface part
- 12b: battery housing part
- 12c: female thread part
- 12d: rib
- 12e: opening
- 12f: recess
- 13: frame body
- 13a: female thread part
- 13b: outer surface
- 15: male thread
- 16: battery
- 17: male thread
- 18: insertion screw
- 20: radiation detector
- 21: scintillator layer
- 22: active-matrix substrate
- 30: protective film
- 31: first protective film
- 31a: end part
- 32: second protective film
- 32a: end part
- 40: radiation shield plate
- 50: support
- 60: radiation shield
- 61: housing part
- 62: radiation shield plate
- 63: attachment member
- 63a: turning shaft
- 70: waterproof structure
- 80: medium plate
- d1: gap
- d2: gap

What is claimed is:

1. A method for manufacturing a housing of a radiation detection cassette that houses a radiation detector in the housing, the method comprising:
   preparing a housing material that is formed of an alloy containing Mg and Li and contains 0.1 mass % or more of Li;
   forming a recess using a working method other than cutting work on a surface of the housing material; and
   performing cutting work on the formed recess to shape the recess,
   wherein the housing material containing Li of 5 mass % or more and 25 mass % or less is prepared.

2. The method for manufacturing a housing of a radiation detection cassette according to claim 1,
   wherein the working method other than the cutting work is press working.

3. The method for manufacturing a housing of a radiation detection cassette according to claim 1,
   wherein the working method other than the cutting work is electrical discharge machining.

4. The method for manufacturing a housing of a radiation detection cassette according to claim 1,
   wherein the working method other than the cutting work is casting.

5. The method for manufacturing a housing of a radiation detection cassette according to claim 1,
   wherein the housing material containing Al is prepared.

6. The method for manufacturing a housing of a radiation detection cassette according to claim 5,
   wherein the housing material containing Al of 1 mass % or more and 12 mass % or less is prepared.

7. The method for manufacturing a housing of a radiation detection cassette according to claim 5,
   wherein the housing material containing Ca is prepared.

8. The method for manufacturing a housing of a radiation detection cassette according to claim 7,
   wherein the housing material containing Ca of 0.3 mass % or more and 7 mass % or less is prepared.

9. The method for manufacturing a housing of a radiation detection cassette according to claim 1,
wherein the housing material containing Ca is prepared.

10. The method for manufacturing a housing of a radiation detection cassette according to claim 9,
wherein the housing material containing Ca of 0.3 mass % or more and 7 mass % or less is prepared.

11. The method for manufacturing a housing of a radiation detection cassette according to claim 1, further comprising:
engaging a frame body with a circumferential edge of the housing material so as to protrude further outward than a position of a side end of the housing material as seen from a radiation exposure side.

12. The method for manufacturing a housing of a radiation detection cassette according to claim 1, further comprising:
engaging a frame body with a circumferential edge of the housing material, and
providing a water-proof structure between the housing material and the frame body.

13. The method for manufacturing a housing of a radiation detection cassette according to claim 1, further comprising:
forming a side peripheral surface part of an inclined surface in the housing material.

14. A for manufacturing a housing of a radiation detection cassette that houses a radiation detector in the housing, the method comprising:
preparing a housing material that is formed of an alloy containing Mg and Li and contains 0.1 mass % or more of Li;
forming a recess using a working method other than cutting work on a surface of the housing material; and
performing a cutting work on the formed recess to shape the recess,
wherein the housing material containing Al is prepared, and
wherein the housing material containing Al of 1 mass % or more and 12 mass % or less is prepared.

15. The method for manufacturing a housing of a radiation detection cassette according to claim 14,
wherein the housing material containing Ca is prepared.

16. The method for manufacturing a housing of a radiation detection cassette according to claim 15,
wherein the housing material containing Ca of 0.3 mass % or more and 7 mass % or less is prepared.

17. The method for manufacturing a housing of a radiation detection cassette according to claim 14,
wherein the working method other than the cutting work is press working.

18. The method for manufacturing a housing of a radiation detection cassette according to claim 14,
wherein the working method other than the cutting work is electrical discharge machining.

19. The method for manufacturing a housing of a radiation detection cassette according to claim 14,
wherein the working method other than the cutting work is casting.

20. The method for manufacturing a housing of a radiation detection cassette according to claim 14, further comprising:
engaging a frame body with a circumferential edge of the housing material so as to protrude further outward than a position of a side end of the housing material as seen from a radiation exposure side.

21. The method for manufacturing a housing of a radiation detection cassette according to claim 14, further comprising:
engaging a frame body with a circumferential edge of the housing material, and
providing a water-proof structure between the housing material and the frame body.

22. The method for manufacturing a housing of a radiation detection cassette according to claim 14, further comprising:
forming a side peripheral surface part of an inclined surface in the housing material.

23. A method for manufacturing a housing of a radiation detection cassette that houses a radiation detector in the housing, the method comprising:
preparing a housing material that is formed of an alloy containing Mg and Li and contains 0.1 mass % or more of Li;
forming a recess using a working method other than cutting work on a surface of the housing material; and
preforming cutting work on the formed recess to shape the recess,
wherein the housing material containing Ca is prepared, and
wherein the housing material containing Ca of 0.3 mass % or more and 7 mass % or less is prepared.

24. The method for manufacturing a housing of a radiation detection cassette according to claim 23,
wherein the working method other than the cutting work is press working.

25. The method for manufacturing a housing of a radiation detection cassette according to claim 23,
wherein the working method other than the cutting work is electrical discharge machining.

26. The method for manufacturing a housing of a radiation detection cassette according to claim 23,
wherein the working method other than the cutting work is casting.

27. The method for manufacturing a housing of a radiation detection cassette according to claim 23, further comprising:
engaging a frame body with a circumferential edge of the housing material so as to protrude further outward than a position of a side end of the housing material as seen from a radiation exposure side.

28. The method for manufacturing a housing of a radiation detection cassette according to claim 23, further comprising:
engaging a frame body with a circumferential edge of the housing material, and
providing a water-proof structure between the housing material and the frame body.

29. The method for manufacturing a housing of a radiation detection cassette according to claim 23, further comprising:
forming a side peripheral surface part of an inclined surface in the housing material.

30. A method for manufacturing a housing of a radiation detection cassette that houses a radiation detector in the housing, the method comprising:
preparing a housing material that is formed of an alloy containing Mg and Li and contains 0.1 mass % or more of Li;
forming a recess using a working method other than cutting work on a surface of the housing material; and
performing cutting work on the formed recess to shape the recess, wherein the housing material containing Al is prepared,
wherein the housing material containing Ca is prepared, and
wherein the housing material containing Ca of 0.3 mass % or more and 7 mass % or less is prepared.

31. The method for manufacturing a housing of a radiation detection cassette according to claim 30,
wherein the working method other than the cutting work is press working.

32. The method for manufacturing a housing of a radiation detection cassette according to claim 30,
wherein the working method other than the cutting work is electrical discharge machining.

33. The method for manufacturing a housing of a radiation detection cassette according to claim 30,
wherein the working method other than the cutting work is casting.

34. The method for manufacturing a housing of a radiation detection cassette according to claim 30, further comprising:
engaging a frame body with a circumferential edge of the housing material so as to protrude further outward than a position of a side end of the housing material as seen from a radiation exposure side.

35. The method for manufacturing a housing of a radiation detection cassette according to claim 30, further comprising:
engaging a frame body with a circumferential edge of the housing material, and
providing a water-proof structure between the housing material and the frame body.

36. The method for manufacturing a housing of a radiation detection cassette according to claim 30, further comprising:
forming a side peripheral surface part of an inclined surface in the housing material.

\* \* \* \* \*